(12) United States Patent
Melde et al.

(10) Patent No.: US 8,993,473 B2
(45) Date of Patent: Mar. 31, 2015

(54) MODIFIED TRILOBE SHAPE FOR MALEIC ANHYDRIDE CATALYST

(75) Inventors: Larry E. Melde, Taylor, TX (US); William A. Smith, Spring, TX (US)

(73) Assignee: Huntsman Petrochemical LLC, The Woodlands, TX (US)

( * ) Notice: Subject to any disclaimer, the term of this patent is extended or adjusted under 35 U.S.C. 154(b) by 921 days.

(21) Appl. No.: 13/123,725

(22) PCT Filed: Oct. 7, 2009

(86) PCT No.: PCT/US2009/059774
§ 371 (c)(1), (2), (4) Date: Apr. 12, 2011

(87) PCT Pub. No.: WO2010/047949
PCT Pub. Date: Apr. 29, 2010

(65) Prior Publication Data
US 2011/0201829 A1   Aug. 18, 2011

Related U.S. Application Data

(60) Provisional application No. 61/106,741, filed on Oct. 20, 2008.

(51) Int. Cl.
| | | |
|---|---|---|
| *B01J 27/14* | (2006.01) | |
| *B01J 27/188* | (2006.01) | |
| *B01J 27/19* | (2006.01) | |
| *B01J 27/192* | (2006.01) | |
| *B01J 27/182* | (2006.01) | |
| *B01J 27/057* | (2006.01) | |
| *B01J 27/185* | (2006.01) | |
| *B01J 27/186* | (2006.01) | |
| *B01J 27/198* | (2006.01) | |
| *B01J 35/00* | (2006.01) | |
| *B01J 35/02* | (2006.01) | |
| *B01J 37/00* | (2006.01) | |
| *C07C 51/215* | (2006.01) | |

(52) U.S. Cl.
CPC .............. *B01J 27/198* (2013.01); *B01J 35/002* (2013.01); *B01J 35/023* (2013.01); *B01J 35/026* (2013.01); *B01J 37/0009* (2013.01); *C07C 51/215* (2013.01); *Y10S 502/52711* (2013.01); *Y10S 502/52714* (2013.01); *Y10S 502/52724* (2013.01)
USPC ........... 502/209; 502/210; 502/211; 502/212; 502/213; 502/214; 502/215; 502/527.11; 502/527.14; 502/527.24

(58) Field of Classification Search
USPC .................. 502/527.11, 527.14, 527.24; 549/257–260, 262; 568/476; 562/545
See application file for complete search history.

(56) References Cited

U.S. PATENT DOCUMENTS 3,856,824 A   12/1974   Raffelson et al.
3,862,146 A   1/1975   Boghosian
(Continued)

FOREIGN PATENT DOCUMENTS

| CN | 2625026 Y | 7/2004 | | |
|---|---|---|---|---|
| EP | 0 098 039 A | 1/1984 | | |
| WO | 2010/047949 | * | 4/2010 | ............ B01J 27/198 |

*Primary Examiner* — Patricia L Hailey
(74) *Attorney, Agent, or Firm* — Huntsman International LLC

(57) ABSTRACT

Embodiments of the present invention include improved shaped catalyst structures containing catalytic material comprised of mixed oxides of vanadium and phosphorus and using such shaped catalyst structures for the production of maleic anhydride.

25 Claims, 3 Drawing Sheets

(56) References Cited

U.S. PATENT DOCUMENTS

| | | |
|---|---|---|
| 3,864,280 A | 2/1975 | Schneider |
| 3,888,866 A | 6/1975 | Leute et al. |
| 3,980,585 A | 9/1976 | Kerr et al. |
| 4,018,709 A | 4/1977 | Barone et al. |
| 4,187,235 A | 2/1980 | Katsumoto et al. |
| 4,251,390 A | 2/1981 | Barone |
| 4,283,307 A | 8/1981 | Barone et al. |
| 4,312,787 A | 1/1982 | Dollyj et al. |
| 4,315,864 A | 2/1982 | Bremer et al. |
| 4,333,853 A | 6/1982 | Milberger et al. |
| 4,562,268 A | 12/1985 | Wrobleski et al. |
| 4,632,915 A | 12/1986 | Keppel et al. |
| 4,652,687 A * | 3/1987 | Imai et al. ............. 585/319 |
| 5,168,090 A | 12/1992 | Ebner et al. |
| 5,275,996 A | 1/1994 | Andrews et al. |
| 8,048,820 B2 * | 11/2011 | Brandstadter et al. ...... 502/209 |
| 2006/0036104 A1 * | 2/2006 | Lu et al. ............. 549/512 |
| 2013/0217897 A1 * | 8/2013 | Shan et al. ............. 549/260 |

\* cited by examiner

MODIFIED TRILOBE SHAPE FOR MALEIC ANHYDRIDE CATALYST

CROSS-REFERENCE TO RELATED APPLICATIONS

This application is the National Phase of International Application PCT/US2009/059774 filed Oct. 7, 2009 which designated the U.S. and which claims priority to U.S. Provisional App. Ser. No. 61/106,741 filed Oct. 20, 2008. The noted applications are incorporated herein by reference.

STATEMENT REGARDING FEDERALLY SPONSORED RESEARCH OR DEVELOPMENT

Not applicable.

BACKGROUND OF THE INVENTION

1. Field of the Invention

The present invention relates generally to producing maleic anhydride and more particularly to shaped catalyst structures containing catalytic material comprised of mixed oxides of vanadium and phosphorus which are useful for the production of maleic anhydride.

2. Background of the Invention

Various shapes for tablets of vanadium and phosphorus catalysts used in the production of maleic anhydride from butane have been described in the literature. For example, U.S. Pat. Nos. 4,283,307 and 5,168,090 describe catalyst tablets of various shapes that are used for the production of maleic anhydride.

One disadvantage of current tablet shapes is that they have relatively low side crush strengths. Side crush strength measures the weight or force needed to break a tablet. The side crush strength is important in catalyst manufacture since it directly impacts the durability of the catalyst during handling, shipment, and installation into a commercial reactor. With all other factors being equal, a catalyst tablet with a higher side crush strength is preferred to one with a lower crush strength.

Another disadvantage of current tablet shapes is that they have relatively high percent attrition. The percent attrition is a measurement (as detailed later) of the amount of catalyst lost to disintegration after subjected to a certain amount of wear and tear. The percent attrition is important in catalyst manufacture since it also directly impacts the durability of the catalyst during handling, shipment, and installation into a commercial reactor. With all other factors being equal, a catalyst tablet with a lower percent attrition is preferred to one with a higher percent attrition.

Catalyst tablets with lower crush strength and higher attrition tend to produce more broken catalyst tablets and more catalyst fines during handling, shipment, and installation into a commercial reactor. These broken catalyst pellets and catalyst fines create increased pressure drop in the commercial reactor tubes during normal operation and are thus undesirable.

BRIEF SUMMARY OF SOME OF THE PREFERRED EMBODIMENTS

Embodiments of the present invention disclose a shaped oxidation catalyst structure for the production of maleic anhydride. The shaped structure contains catalytic material comprised of mixed oxides of vanadium and phosphorus. The shaped structure has a solid cylinder structure, wherein the cylinder structure has a cylinder height and a cylinder radius. The solid cylinder structure has three void spaces running along the cylinder height to form three lobes. Each lobe has a corner that is defined by a lobe radius. For the shaped structure, the ratio of the cylinder radius over the lobe radius is equal to or less than about 15.

Embodiments of the present invention include a process for preparing maleic anhydride. A hydrocarbon having at least four carbons in a straight chain is reacted with a molecular oxygen-containing gas in the presence of a shaped oxidation catalyst structure according to this invention.

Embodiments of the present invention include maleic anhydride produced by the process of reacting a hydrocarbon having at least four carbons in a straight chain with a molecular oxygen-containing gas in the presence of a shaped oxidation catalyst structure according to this invention.

The foregoing has outlined rather broadly the features of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments. The units of measure in these drawings are in inches.

DETAILED DESCRIPTION OF THE PREFERRED EMBODIMENTS

Figure 1A:
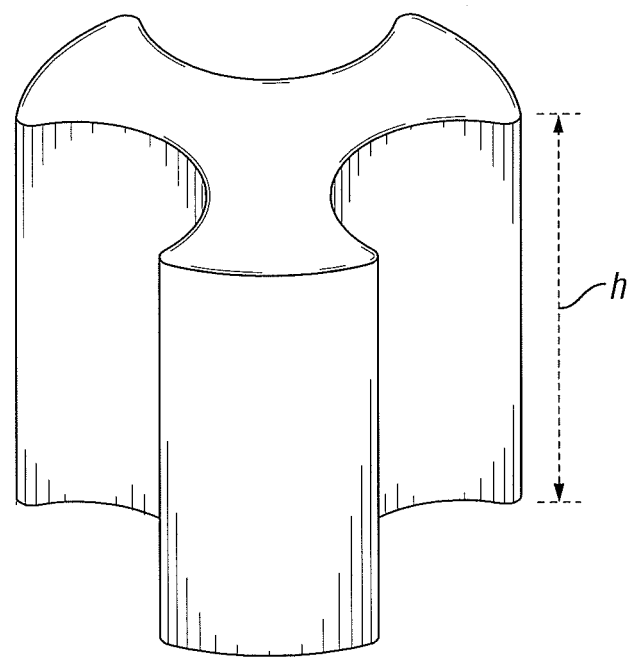
FIG. 1A illustrates a current trilobe tablet that is a solid cylinder structure having three void spaces running along the height of the cylinder.
Figure 1B:
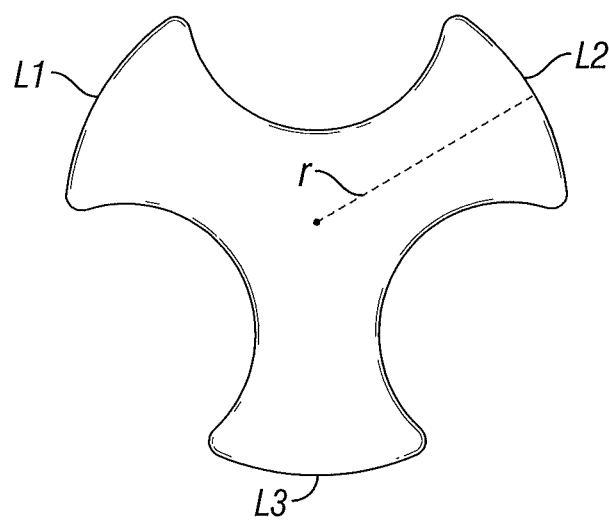
FIG. 1B illustrates, in top elevational view, a current trilobe tablet.

FIGS. 1A, 1B, 1C and 3A show the current trilobe tablet. The trilobe tablet is a solid cylinder structure of height "h" (FIG. 1A) and of cylinder radius "r" (FIG. 1B). The solid cylinder structure has three void spaces running along the cylinder height to form three lobes L1, L2 and L3 (FIG. 1B).

Figure 1C:
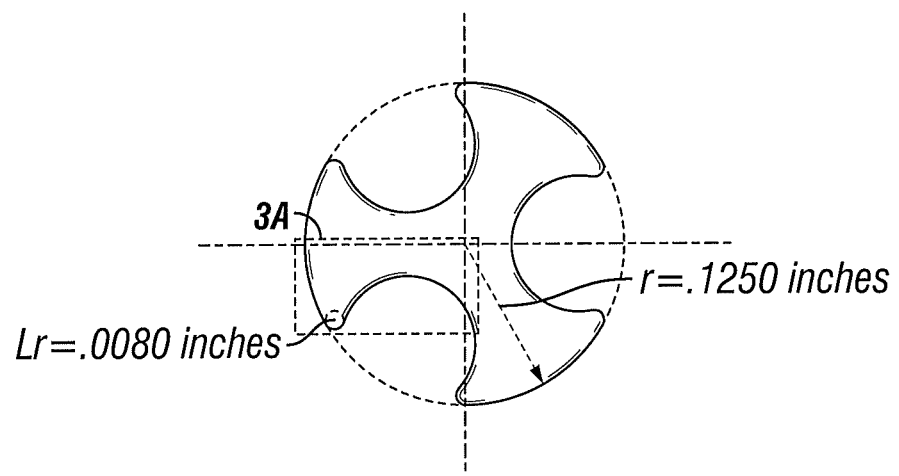
FIG. 1C illustrates, in top elevational view, a current trilobe tablet with its cylinder radius and lobe radius.

Each lobe has a corner that has a shape that is defined by a lobe radius "Lr" (0.0080 RAD in FIG. 1C).

It has now been surprisingly found that trilobe tablets have improved side crush strengths, lower percent attrition, and better packing density (leading to improved catalytic performance) if the lobe radii have been lengthened so that the ratio of the cylinder radius over the lobe radius is equal to or less than about 15. By the term "improved catalytic performance" it is meant there is an improvement in at least one of the catalyst properties, which properties include yield, selectivity, conversion; yield, selectivity or conversion performance over time, loading characteristics and operability. These results are unexpected in view of the prior teachings which relate to catalyst structures. Namely, one skilled in the art would expect that the lengthening of lobe radii would result in roughly equivalent crush strengths and percent attritions and possibly adversely affect the catalytic performance of such catalysts because of reduced surface areas.

Figure 2:
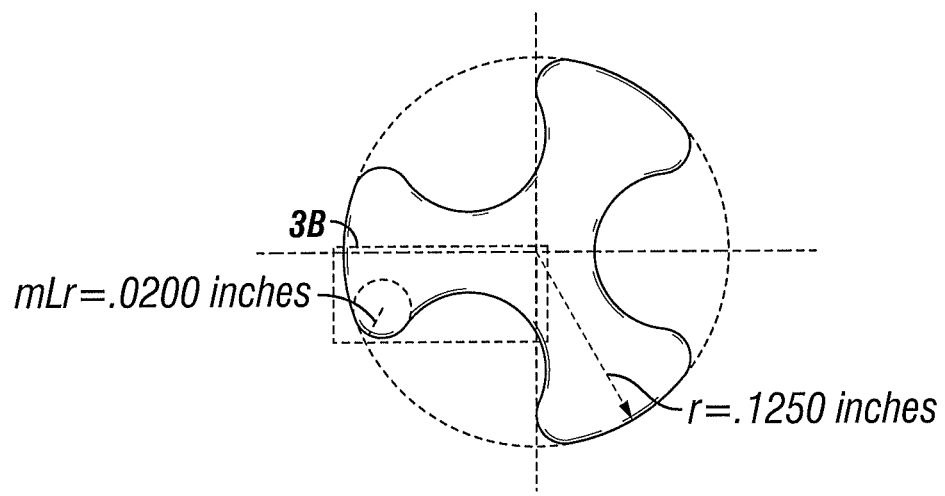
FIG. 2 illustrates, in top elevational view, a modified trilobe tablet of the present invention, with its cylinder radius and modified lobe radius.
Figure 3A:
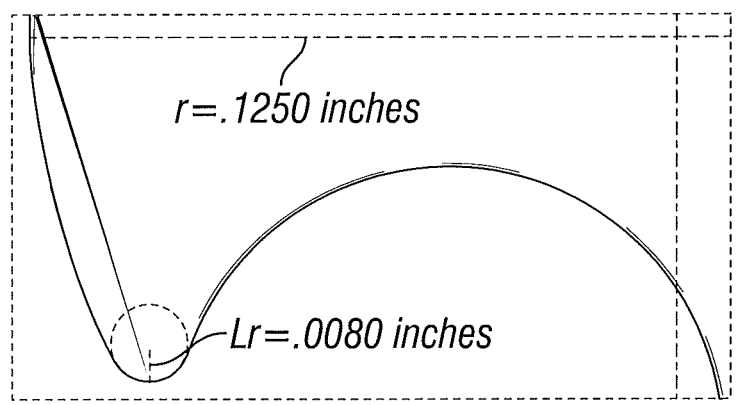
FIG. 3A illustrates, in top elevational view, a magnified region of the current trilobe tablet, with its cylinder radius and lobe radius more clearly defined.
Figure 3B:
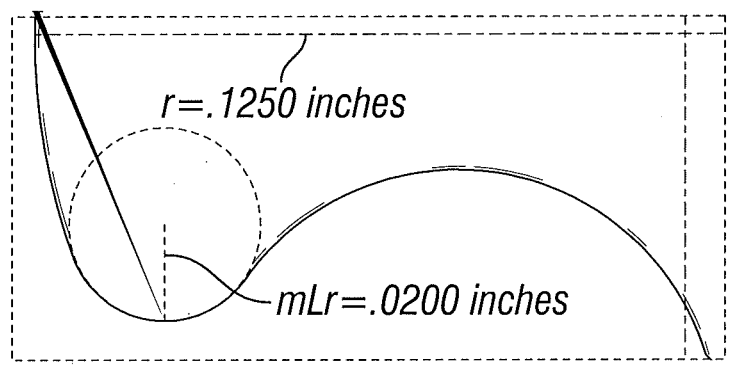
FIG. 3B illustrates, in top elevational view, a magnified region of the modified trilobe tablet of the present invention, with its cylinder radius and modified lobe radius more clearly defined.

An embodiment of the present invention is illustrated in FIG. 2. FIG. 2 shows a modified trilobe tablet where the lobe radius is lengthened. FIG. 2 shows a modified trilobe tablet with a modified lobe radius (mLr) of 0.0200, which is two and a half times the lobe radius (Lr=0.0080) in FIG. 1C. FIGS. 3A and 3B allow for closer comparison a clarification of the comparisons of lobe radii. Lengthening the lobe radius results in a modified trilobe tablet that has a more open and smoothed shape.

Embodiments of the present invention have a ratio of the cylinder radius over the lobe radius is equal to or less than about 15. In other embodiments, this ratio is equal to or less than about 14, 13, 12, 11, 10, 9, 8, 7, 6, 5, 4 or 3. In another embodiment, this ratio is about 6.25. One skilled in the art, with the benefit of this disclosure, will recognize appropriate ratios to use in embodiments of the present invention.

Embodiments of the present invention include shaped structures that have an attrition of less than about 10%. In other embodiments, the attrition of the shaped structures is less than about 11%, 12%, 13%, 14% or 15%. The attrition measurement is described in detail in the Examples section.

Embodiments of the present invention include shaped structures that have a side crush strength greater than about 10 pounds. In other embodiments, the shaped structures have a side crush strength greater than about 15, 16, 17, 18, 19 or 20 pounds. The side crush strength measurement technique is described in the Examples section.

The shaped structures of embodiments of the present invention contains catalytic material comprised of mixed oxides of vanadium and phosphorus. Catalyst materials suitable for use in the instant invention are those known to the art, and in general are materials capable of catalyzing the vapor phase partial oxidation of hydrocarbons to maleic anhydride under oxidation conditions. Such materials in general comprise a vanadium phosphorus oxide complex, optionally further comprising a promoter element. A convenient, albeit nonlimiting, representation of an empirical formula for suitable catalytic material may be expressed as $VP_xO_yM_z$ wherein M is at least one promoter element selected from the group consisting of elements from Groups IA, IB, IIA, IIB, IIIA, IIIB, IVA, IVB, VA, VB, VIB, and VIIIB of the Periodic Table of the Elements, x is a number from about 0.5 to about 2.0, preferably from about 0.95 to about 1.35, y is a number taken to satisfy the valences of V, P, and M in the oxidation states in which they exist in the composition, and z is a number from zero (0) to about 1.0, preferably up to about 0.5. The term "Periodic Table of the Elements", as employed herein, refers to the Periodic Table of the Elements published in The Merck Index, 10th ed., Windholtz, Ed., Merck & Co., Inc., Rahway, N.J., 1983, Inside Front Cover.

Specific, albeit nonlimiting, examples of suitable catalyst materials are those described in U.S. Pat. Nos. 4,632,915; 4,562,268; 4,333,853; 4,315,864; 4,312,787; 4,251,390; 4,187,235; 4,018,709; 3,980,585; 3,888,866; 3,864,280; 3,862,146; and 3,856,824; and European Patent Application No. 98,039—it being understood, however, that the same are not to be construed as limiting but instead are for purposes of illustration and guidance in the practice of the instant invention. These references are herein incorporated by reference. Among such catalyst materials, those in general preferred for use in the instant invention are those described in U.S. Pat. Nos. 4,632,915, 4,562,268, and 5,275,996.

The shaped oxidation catalyst structures of the instant invention may be prepared by blending the catalyst material with shaped structure forming aids known to the art such as graphite or stearic acid and any desirable inert filler material and pressing or compacting in a mold (tableting press equipped with an appropriate die and punch) or by extrusion or casting in accordance with procedures known in the art. In general, the compaction technique is preferred in that shaped structures exhibiting characterizing properties in accordance with the instant invention are more readily obtained. In a similar manner, the absence of the employment of inert filler material is preferred in that the partial oxidation reaction of hydrocarbon to maleic anhydride is advantageously carried out in a manner which maximizes the amount of active catalyst material contained in the specified volume of the reactor to thereby maximize the amount of hydrocarbon converted in a single reactor pass.

Embodiments of the present invention disclose processes to produce maleic anhydride. In one embodiment, a process for preparing maleic anhydride is disclosed that comprises the step of reacting a hydrocarbon having at least four carbons in a straight chain with a molecular oxygen-containing gas in the presence of a shaped oxidation catalyst structure that contains catalytic material comprised of mixed oxides of vanadium and phosphorus and has a solid cylinder structure, wherein the cylinder structure has a cylinder height and a cylinder radius, and the solid cylinder structure has three void spaces running along the cylinder height to form three lobes, wherein each lobe has a corner that is defined by a lobe radius, wherein the ratio of the cylinder radius over the lobe radius is equal to or less than about 15.

The shaped oxidation catalyst structures of the instant invention are useful in a variety of reactors to convert non-aromatic hydrocarbons to maleic anhydride. A typically satisfactory reactor is a tube-shell fixed-bed (tubular) with heat exchanger-type reactor. The details of operation of such reactors are well known to those skilled in the art. The tubes of such reactors can be constructed of iron, stainless steel, carbon steel, nickel, glass, such as Vycor, and the like and can vary in diameter from about 0.635 cm (0.25 in.) to about 3.81 cm (1.50 in.) and the length can vary from about 15.24 cm (6 in.) to about 762 cm (25 ft). The oxidation reaction is highly exothermic and once reaction is underway, in order to maintain the desired reactor temperature, a heat transfer medium is necessary to conduct heat away from the reactor. Suitable heat transfer media are well known to those skilled in the art and, in general, are materials that remain in the liquid state at process temperatures and have a relatively high thermal conductivity. Examples of useful media include various heat transfer oils, molten sulfur, mercury, molten lead, and salts such as nitrates and nitrites of alkali metals, the salts being preferred due to their high boiling points. A particularly preferred heat transfer medium is a eutectic mixture of potassium nitrate, sodium nitrate and sodium nitrite which not only has a desirably high boiling point, but also, a sufficiently low freezing point that it remains in a liquid state even during periods of reactor shutdown. An additional method of temperature control is to use a metal block reactor whereby the metal surrounding the reaction zone of the reactor acts as a temperature regulating body or by conventional heat exchangers.

In general, the reaction to convert nonaromatic hydrocarbons to maleic anhydride using the shaped oxidation catalyst structures of the instant invention involves charging a mixture of a nonaromatic hydrocarbon having at least four (4) carbon atoms in a straight chain (or in a cyclic structure) and a molecular oxygen-containing gas (including molecular oxygen, itself), such as air or molecular oxygen-enriched air, to a heat transfer medium-cooled reactor or reaction zone packed with the shaped oxidation catalyst structures of the instant invention to contact the hydrocarbon/molecular oxygen-containing gas mixture with the catalyst at elevated temperatures. In addition to the hydrocarbon and molecular oxygen, other gases, such as nitrogen or steam, may be present or added to the reactant feedstream. Typically, the hydrocarbon is admixed with the molecular oxygen-containing gas, preferably air, at a concentration of from about 1 mol % to about 10 mol % hydrocarbon and contacted with the catalyst at a gas hourly space velocity (GHSV), or simply space velocity, of from about 100 $hr^{-1}$ up to about 5,000 $hr^{-1}$ and at a temperature of from about 300° C. to about 600° C., preferably from about 1,000 $hr^{-1}$ to about 3,000 $hr^{-1}$ and from about 325° C. to about 450° C. to produce maleic anhydride.

The initial yield of maleic anhydride, however, may be low. And if this is the case, the catalyst, as will occur to those skilled in the art, can be "conditioned" by contacting the shaped oxidation catalyst structures of the instant invention with low concentrations of hydrocarbon and molecular oxygen-containing gas at low space velocities for a period of time before production operations begin.

Pressure is not critical in the reaction to convert nonaromatic hydrocarbons to maleic anhydride. The reaction may be conducted at atmospheric, superatmospheric, or subatmospheric pressure. It generally will be preferred, however, for practical reasons, to conduct the reaction at or near atmospheric pressure. Typically, pressures of from about 1.013× $10^2$ kilopascals-gauge (kPa-g, 14.7 psig, 1 atm) to about 3.45×$10^2$ kPa-g (50.0 psig), preferably from about 1.24×$10^2$ kPa-g (18.0 psig) to about 2.068×$10^2$ kPa-g (30.0 psig), may be conveniently employed.

Maleic anhydride produced by using the shaped oxidation catalyst structures of the instant invention can be recovered by any means known to those skilled in the art. For example, maleic anhydride can be recovered by direct condensation or by absorption in suitable media with subsequent separation and purification of the maleic anhydride.

A large number of nonaromatic hydrocarbons having from four to ten carbon atoms can be converted to maleic anhydride using the shaped oxidation catalyst structures of the instant invention. It is only necessary that the hydrocarbon contain not less than four carbon atoms in a straight chain or in a cyclic ring. As an example, the saturated hydrocarbon n-butane is satisfactory, but isobutane (2-methylpropane) is not satisfactory for conversion to maleic anhydride although its presence is not harmful. In addition to n-butane, other suitable saturated hydrocarbons include the pentanes, the hexanes, the heptanes, the octanes, the nonanes, the decanes, and mixtures of any of these, with or without n-butane, so long as a hydrocarbon chain having at least four carbon atoms in a straight chain is present in the saturated hydrocarbon molecule.

Unsaturated hydrocarbons are also suitable for conversion to maleic anhydride using the shaped oxidation catalyst structures of the instant invention. Suitable unsaturated hydrocarbons include the butenes (1-butene and 2-butene), 1,3-butadiene, the pentenes, the hexenes, the heptenes, the octenes, the nonenes, the decenes, and mixtures of any of these, with or without the butenes, again, so long as the requisite hydrocarbon chain having at least four carbon atoms in a straight chain is present in the molecule.

Cyclic hydrocarbons such as cyclopentane and cyclopentene also are satisfactory feed materials for conversion to maleic anhydride using the shaped oxidation catalyst structures of the instant invention. Aromatic hydrocarbons such as benzenes are satisfactory feed materials.

Of the aforementioned feedstocks, n-butane is the preferred saturated hydrocarbon and the butenes are the preferred unsaturated hydrocarbons, with n-butane being most preferred of all feedstocks. Mixtures of the aforementioned feedstocks are satisfactory feed materials.

It will be noted that the aforementioned feedstocks need not necessarily be pure substances, but can be technical grade hydrocarbons.

The principal product from the oxidation of the aforementioned suitable feed materials is maleic anhydride, although small amounts of citraconic anhydride (methyl maleic anhydride) also may be produced when the feedstock is a hydrocarbon containing more than four carbon atoms.

Embodiments of the present invention also disclose maleic anhydride produced by the process of reacting a hydrocarbon having at least four carbons in a straight chain with a molecular oxygen-containing gas in the presence of a shaped oxidation catalyst structure, the shaped structure containing catalytic material comprised of mixed oxides of vanadium and phosphorus; and having a solid cylinder structure, wherein the cylinder structure has a cylinder height and a cylinder radius, and the solid cylinder structure has three void spaces running along the cylinder height to form three lobes, wherein each lobe has a corner that is defined by a lobe radius, wherein the ratio of the cylinder radius over the lobe radius is equal to or less than about 15.

The following specific examples illustrating the best currently-known method of practicing this invention are described in detail in order to facilitate a clear understanding of the invention. It should be understood, however, that the detailed expositions of the application of the invention, while indicating preferred embodiments, are given by way of illustration only and are not to be construed as limiting the invention since various changes and modifications within the spirit of the invention will become apparent to those skilled in the art from this detailed description.

EXAMPLES

Catalyst tablets in both the current trilobe shape and the modified trilobe shape were made from vanadium pyrophosphate powder in the manner described below. The side crush strength and the percent attrition were measured for both tablet shapes.

Vanadium pyrophosphate catalyst powder was made in the normal manner according to U.S. Pat. No. 5,275,996, entitled "Phosphorous/Vanadium Oxide Catalyst and Process of Preparation Thereof." This powder was formed into catalyst tablets using a standard laboratory catalyst tabletting machine. Different dies were used in the tabletting machine to produce different shapes of catalyst tablets. One batch of tablets were made using the current trilobe dies and another batch of tablets were made using the modified trilobe dies.

A LTCM-6 w/DFM 100 crush strength system from Chatillon Force Measurement Systems was used for side crush strength measurement. The average side crush strength (lbs) for the current trilobe tablet was 8.1 lbs which is typical for this catalyst formulation and catalyst shape. The average side crush strength (lbs) for the modified trilobe tablet was 27.8 lbs, more than triple that of the current trilobe shape. As can be seen from the data, there was a surprisingly significant increase in the side crush strength for the modified trilobe tablets.

The percent attrition was measured for both the current trilobe tablet and the modified trilobe tablet. The attrition is measured using a rotating cylindrical drum that had a 10 inch (254 mm) diameter and a 6 inch (152 mm) height with a single radial baffle 2 inches (51 mm) high extending the full height of the cylinder. The inside of the drum had a surface roughness no greater than about 250μ inch (6.4 μm). About 110 g of the sample catalyst tablets were gently sieved through a #20 (850 micrometer (μm)) sieve. The presieved catalyst tablets were transferred to a wide-mouth container tared to the nearest 0.01 g. The test cylinder and lid of the apparatus were cleaned using a fine-bristle brush. About 100 g of the presieved catalyst tablets were weighted to the nearest 0.01 g and recorded as weight "A." The weighed presieved catalyst tablets were then transferred into the drum which was carefully sealed for rotation. The drum was rotated for 1800 revolutions at a rate of 60+5 revolutions per minute (rpm). A #20 (850 μm) sieve with pan was placed under the drum and the cover was carefully removed. The drum contents were poured onto the sieve using a fine-bristle brush to clean out the drum and its cover. The fines were sieved into the pan by gently shaking the sieve by hand; avoiding excessive agitation. Fines produced by attrition and abrasion in the test where weighed to the nearest 0.01 g and this weight was recorded as "B." The percent loss on attrition was calculated as follows:

Loss on attrition, $\% = (A-B)/A \times 100$

When the loss on attrition is less than 1.0%, it should be reported as "less than 1%. For this test method, the percent attrition indicates the weight percentage of catalyst fines generated during the test that are smaller than about 850μ in diameter.

The percent attrition for the current trilobe shape was 14.4% which is typical for this catalyst formulation and catalyst shape. The percent attrition for the modified trilobe shape was 9.27%. As can be seen from the data, there was a surprisingly significant decrease in the percent attrition for the modified trilobe tablets by roughly 40%.

Preliminary packing data indicates that the modified trilobe shape allows for greater density of catalyst in the reactor tube than the current trilobe shape. The greater density of catalyst results in improved catalyst loading per reactor tube.

Although the present invention and its advantages have been described in detail, it should be understood that various changes, substitutions and alterations may be made herein without departing from the spirit and scope of the invention as defined by the appended claims.

What is claimed is:

1. A shaped oxidation catalyst structure for the production of maleic anhydride, the shaped structure comprising:
   a catalytic material comprised of mixed oxides of vanadium and phosphorus; and
   a solid cylinder structure, wherein the cylinder structure has a cylinder height and a cylinder radius, and the solid cylinder structure has three void spaces running along the cylinder height to form three lobes, wherein each lobe has a corner that is defined by a lobe radius, wherein the ratio of the cylinder radius over the lobe radius is equal to or less than about 15.

2. The shaped oxidation catalyst structure of claim 1 wherein the ratio of the cylinder radius over the lobe radius is equal to or less than about 12.

3. The shaped oxidation catalyst structure of claim 1 wherein the ratio of the cylinder radius over the lobe radius is equal to or less than about 10.

4. The shaped oxidation catalyst structure of claim 1 wherein the ratio of the cylinder radius over the lobe radius is equal to or less than about 8.

5. The shaped oxidation catalyst structure of claim 1 wherein the ratio of the cylinder radius over the lobe radius is about 6.25.

6. The shaped oxidation catalyst structure of claim 1 wherein the shaped structure has an attrition of less than about 10%.

7. The shaped oxidation catalyst structure of claim 1 wherein the shaped structure has a side crush strength greater than about 10 pounds.

8. The shaped oxidation catalyst structure of claim 1 wherein the shaped structure has a side crush strength greater than about 15 pounds.

9. The shaped oxidation catalyst structure of claim 8, wherein the shaped structure has an attrition of less than about 10%.

10. The shaped oxidation catalyst structure of claim 9, wherein each lobe has two corners.

11. The shaped oxidation catalyst structure of claim 1 wherein the shaped structure has a side crush strength greater than about 20 pounds.

12. The shaped oxidation catalyst structure of claim 1 wherein the catalytic material is represented by the empirical formula: $VP_xO_yM_z$; wherein M is at least one promoter element selected from the group consisting of elements from Groups IA, IB, IIA, IIB, IIIA, IIIB, IVA, IVB, VA, VB, VIB, and VIIIB of the Periodic Table of the Elements, x is a number from about 0.5 to about 2.0, y is a number taken to satisfy the valences of V, P, and M in the oxidation states in which they exist in the composition, and z is a number from zero (0) to about 1.0.

13. The shaped oxidation catalyst structure of claim 12 wherein x is a number from about 0.95 to about 1.35 and z is a number up to about 0.5.

14. The shaped oxidation catalyst structure of claim 12 wherein M is selected from the group consisting of elements from Groups IA and IIB of the Periodic Table of the Elements.

15. The shaped oxidation catalyst structure of claim 14 wherein M from Group IA is lithium and from Group IIB is zinc.

16. The shaped oxidation catalyst structure of claim 12 wherein M is selected from the group consisting of elements from Groups IA and VIIIB of the Periodic Table of the Elements.

17. The shaped oxidation catalyst structure of claim 16 wherein M from Group IA is lithium and from Group VIIIB is iron.

18. The shaped oxidation catalyst structure of claim 1, wherein each lobe has two corners.

19. A process for preparing maleic anhydride comprising the step of reacting a hydrocarbon having at least four carbons in a straight chain with a molecular oxygen-containing gas in the presence of a shaped oxidation catalyst structure, the shaped structure comprising:
   a catalytic material comprised of mixed oxides of vanadium and phosphorus; and a solid cylinder structure, wherein the cylinder structure has a cylinder height and a cylinder radius, and the solid cylinder structure has three void spaces running along the cylinder height to form three lobes, wherein each lobe has a corner that is defined by a lobe radius, wherein the ratio of the cylinder radius over the lobe radius is equal to or less than about 15.

20. The process according to claim 19 wherein the hydrocarbon is selected from the group consisting of a saturated hydrocarbon, an unsaturated hydrocarbon, a cyclic hydrocarbon, an aromatic hydrocarbon and a mixture thereof.

21. The process according to claim 19 wherein the hydrocarbon is selected from n-butane, 1-butene, 2-butene, benzene and a mixture thereof.

22. The process according to claim 19 wherein the reaction occurs at a temperature ranging from about 300° C. to about 600° C., a space velocity ranging from about 100 hr$^{-1}$ to about 5000 hr$^{-1}$, and a pressure ranging from subatmospheric pressure to superatmospheric pressure.

23. The process according to claim 19 wherein the reaction occurs at a temperature ranging from about 325° C. to about 450° C., a space velocity ranging from about 1000 hr$^{-1}$ to 3000 hr$^{-1}$ and a pressure ranging from about 1.013×10$^2$ kPa-gauge to about 3.45×10$^2$ kPa-gauge.

24. The process according to claim 19, wherein the each lobe has two corners.

25. Maleic anhydride produced by the process of reacting a hydrocarbon having at least four carbons in a straight chain with a molecular oxygen-containing gas in the presence of a shaped oxidation catalyst structure, the shaped structure being characterized by: (1) containing catalytic material comprised of mixed oxides of vanadium and phosphorus; and (2) having a solid cylinder structure, wherein the cylinder structure has a cylinder height and a cylinder radius, and the solid cylinder structure has three void spaces running along the cylinder height to form three lobes, wherein each lobe has a corner that is defined by a lobe radius, wherein the ratio of the cylinder radius over the lobe radius is equal to or less than about 15.

* * * * *